United States Patent [19]

Poittevin et al.

[11] 4,108,994

[45] Aug. 22, 1978

[54] 5-THIAZOLE-METHANE-AMINES, AND THEIR USE AS ANTILIPOLYTICS

[75] Inventors: André Poittevin, Vaires-sur-Marne; Pierre Henri Derible, Le Perreux; Robert Fournex, Paris, all of France

[73] Assignee: Roussel Uclaf, Paris, France

[21] Appl. No.: 721,370

[22] Filed: Sep. 8, 1976

[30] Foreign Application Priority Data

Sep. 12, 1975 [FR] France .................................. 75 28095
Mar. 31, 1976 [FR] France .................................. 76 09337

[51] Int. Cl.$^2$ .................. C07D 277/38; A61K 31/425
[52] U.S. Cl. .................................... 424/250; 424/251; 424/267; 424/270; 260/302 R; 260/293.68; 544/238; 544/369; 544/333
[58] Field of Search ........ 260/302 R, 293.68, 256.5 R, 260/250 A; 268/268 H; 424/270, 267, , 250, 251

[56] References Cited

PUBLICATIONS

Buchman et al., Chem. Abstracts, 39:1873 (1945).
Wagner et al., Synthetic Organic Chemistry, Wiley, N.Y., 1953, pp. 666–670 & 679–680.
Zubarovskii et al., Chem. Abstracts, 58:2525 (1963).

*Primary Examiner*—Nicholas S. Rizzo

*Attorney, Agent, or Firm*—Hammond & Littell

[57] ABSTRACT

A 5-thiazole-methane-amine selected from the group consisting of (1) compounds having the formula

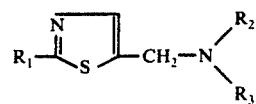

wherein $R_1$ represents an alkyl having from 1 to 6 carbon atoms and $R_2$ and $R_3$ represent members selected from the group consisting of hydrogen, alkyl having from 1 to 6 carbon atoms, hydroxyalkyl having 1 to 6 carbon atoms, and, taken together, alkylene having up to 5 carbon atoms, azaalkylene having up to 4 carbon atoms, alkylalkylene having up to 5 carbon atoms in the alkylene and 1 to 4 carbon atoms in the alkyl, and alkylazaalkylene having up to 4 carbon atoms in the azaalkylene and 1 to 4 carbon atoms in the alkyl which may be in any position, and (2) its acid addition salts with non-toxic, pharmaceutically-acceptable acids; as well as processes for the preparation of the compounds and a process for use of the compounds as an antilipolytic agent.

14 Claims, No Drawings

5-THIAZOLE-METHANE-AMINES, AND THEIR USE AS ANTILIPOLYTICS

RELATED ART

U.S. Pat. No. 3,882,110 discloses 2-alkyl-5-thiazole carboxylates useful as hypolipemiants. U.S. Pat. No. 3,957,809 discloses 2-alkyl-5-thiazole-methylol and its ethers and esters as hypolipemiants. U.S. patent application Ser. Nos. 654,629, 654,514, 654,630, filed Feb. 2, 1976 and 659,760, filed Feb, 20, 1976, all commonly assigned, disclose various antipolytic agents having thiazole rings substituted in the 2 position by an alkyl and in the 5 position by various substituents.

OBJECTS OF THE INVENTION

An object of the present invention is the production of a 5-thiazole-methane-amine selected from the group consisting of (1) compounds having the formula

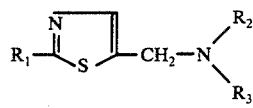

wherein $R_1$ represents an alkyl having from 1 to 6 carbon atoms and $R_2$ and $R_3$ represent members selected from the grop consisting of hydrogen, alkyl having from 1 to 6 carbon atoms, hydroxyalkyl having 1 to 6 carbon atoms, and, taken together, alkylene having up to 5 carbon atoms, azaalkylene having up to 4 carbon atoms, alkylalkylene having up to 5 carbon atoms in the alkylene and 1 to 4 carbon atoms in the alkyl, and alkylazaalkylene having up to 4 carbon atoms in the azaalkylene and 1 to 4 arbon atoms in the alkyl which may be in any position and (2) its acid addition salts with non-toxic, pharmaceutically acceptable acids.

Another object of the present invention is the development of processes to produce the above 5-thiazole-methane-amines.

A further object of the present invention is the antilipolytic compositions containing an effective amount of the above 5-thiazole-methane-amines.

A still further object of the present invention is the development of a process for the treatment of hyperlipemia and of diabetes in warm-blooded animals by administration of an effective amount of the above 5-thiazole-methane-amines.

These and other objects of the invention will become apparent as the description thereof proceeds.

DESCRIPTION OF THE INVENTION

The present invention relates to derivatives of 5-thiazole-methane-amine of the general formula I:

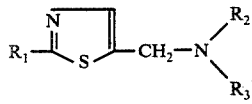   I in which $R_1$ represents an alkyl having from 1 to 6 carbon atoms, $R_2$ and $R_3$, the same or different, represent hydrogen, alkyl having from 1 to 6 carbon atoms, alkyl having from 1 to 6 carbon atoms substituted by a hydroxy group, or both $R_2$ and $R_3$ form, together with the nitrogen atom to which they are attached, a saturated heterocycle containing, optionally, another nitrogen atom, the said heterocycle can also be substituted by an alkyl having from 1 to 4 carbon atoms.

The products of formula I, such as defined above, and their acid addition salts with non-toxic, pharmaceutically-acceptable mineral or organic acids possess interesting pharmacological properties. They manifest a marked antilipolytic activity and decrease the level of plasmatic free fatty acids in the blood. They also have a more or less important hypoglycemiant activity.

A 5-thiazole-methane-amine selected from the group consisting of (1) compounds having the formula

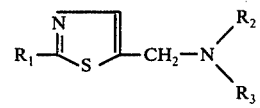

wherein $R_1$ represents an alkyl having from 1 to 6 carbon atoms and $R_2$ and $R_3$ represents members selected from the group consisting of hydrogen, alkyl having from 1 to 6 carbon atoms, hydroxyalkyl having 1 to 6 carbon atoms, and, taken together, alkylene having up to 5 carbon atoms, azaalkylene having up to 4 carbon atoms, alkylalkylene having up to 5 carbon atoms in the alkylene and 1 to 4 carbon atoms in the alkyl, and alkylazaalkylene having up to 4 carbon atoms in the azaalkylene and 1 to 4 carbon atoms in the alkyl which may be in any position, and (2) its acid addition salts with non-toxic, pharmaceutically acceptable acids.

The alkyl having from 1 to 6 carbon atoms for either $R_1$, $R_2$ or $R_3$ can designate methyl, ethyl, n-propyl, isopropyl, n-butyl, isobutyl, tert.-butyl, pentyl, hexyl, for example. The hydroxyalkyl having 1 to 6 carbon atoms can be hydroxyethyl, hydroxypropyl, for example.

The heterocyclic radical which is formed by $R_2$ and $R_3$ together with the nitrogen atom can be, for example, pyrrolidin-1-yl, imidazolidin-1-yl, 3-methyl-imidazolidin-1-yl, 3-ethyl-imidazolidin-1-yl, pyrazolidin-1-yl, 2-methyl-pyrazolidin-1-yl, piperidin-1-yl, piperazin-1-yl, 4-methyl-piperazin-1-yl, 4-ethyl-piperazin-1-yl, 4-propyl-piperazin-1-yl, 4-butyl-piperazin-1-yl, hexahydro-pyridazin-1-yl, 2-methyl-hexahydro-pyridazin-1-yl, hexahydro-pyrimidin-1-yl, 3-methyl-hexahydro-pyrimidin-1-yl, etc.

The acid addition salts which are also an object of the invention can be the salts of any organic or mineral acid, preferably the non-toxic, pharmaceutically-acceptable acids. These salts can be formed from strong mineral acids such as hydrochloric acid, hydrobromic acid, hydroiodic acid, nitric acid, sulfuric acid, phosphonic acid, etc., or organic acids such as lower alkanoic acids, for example, acetic acid, lower alkanedioic acids, for example, oxalic acid, succinic acid, lower alkenedioic acids, for example, maleic acid, fumaric acid, lower alkanepolyoic acids, for example, tartaric acid, lower alkanemonosulfonic acids, for example, methanesulfonic acid, ethanesulfonic acid, propanesulfonic acid, lower alkanedisulfonic acids, for example, methanedisulfonic acid, $\alpha,\beta$-ethanedisulfonic acid, $\alpha,\beta$-propanedisulfonic acid, arylmonosulfonic acids, for example, benzenesulfonic acid, toluenesulfonic acid, and aryldisulfonic acids.

The 5-thiazole-methane-amine of formula I can form the acid salt by one equivalent of the acid, or when the acid employed is sufficiently strong, by two equivalents of the acid. For example, a hemisuccinate or a nitrate salt of the product of formula I can be obtained, which are the salts corresponding to salt formation by one equivalent of acid. Equally, for example, a dinitrate of the product of formula I can be obtained, corresponding to salt formation by two equivalents of acid.

From among the products of formula I and their salts, the following are of particular importance:

(1) the products as defined above characterized in that, in formula I, $R_2$ and $R_3$, either the same or different represent hydrogen, methyl, ethyl or hydroxyethyl, as well as their salts;

(2) the products as defined above characterized in that, in formula I, $R_1$ represents methyl, ethyl or propyl, and $R_2$ and $R_3$, either the same or different, represent hydrogen or methyl, as well as their salts;

(3) the products as defined above characterized in that, in formula I, $R_2$ and $R_3$ together with the nitrogen atom represent a saturated heterocycle and particularly piperidin-1-yl and 4-methyl-piperazin-1-yl, as well as their salts.

The products of primary importance are:

(a) the hemisuccinate of 2-methyl-5-thiazole-methane-amine ($R_1 = CH_3$, $R_2 = R_3 = H$)

(b) the acetate of N,2-dimethyl-5-thiazole-methane-amine ($R_1 = R_2 = CH_3$, $R_3 = H$)

(c) the maleate of N,N,2-trimethyl-5-thiazole-methane-amine ($R_1 = R_2 = R_3 = CH_3$)

(d) the dinitrate of N,N-bis-($\beta$-hydroxyethyl)-2-methyl-5-thiazole-methane-amine ($R_1 = CH_3$, $R_2 = R_3 = CH_2CH_2OH$)

(e) the hemisuccinate of 2-n-propyl-5-thiazole-methane-amine ($R_1 = CH_2CH_2CH_3$, $R_2 = R_3 = H$)

(f) the hemiethanedisulfonate of 2-methyl-5-(piperidin-1-yl-methyl)-thiazole ($R_1 = CH_3$, $R_2 + R_3 = CH_2-CH_2-CH_2-CH_2-CH_2-$)

(g) the 2-methyl-5-(4-methyl-piperazin-1-yl)-thiazole $$(R_1 = CH_3, R_2 + R_3 = -CH_2-CH_2-\overset{\overset{CH_3}{|}}{N}-CH_2-CH_2-).$$

The invention also encompasses the processes for the production of the substituted 5-thiazole-methane-amines.

(A) Compounds of formula I, as well as their acid addition salts with mineral or organic acids, in which $R_2$ and $R_3$ are hydrogen, can be prepared by reacting a product having the formula II

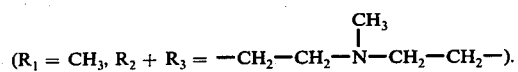

II in which $R_1$ represents alkyl having from 1 to 6 carbon atoms and X represents a halogen selected from the group consisting of chlorine and bromine, or one of its acid addition salts with a strong mineral or organic acid, either with hexamethylene tetramine, in order to obtain a complex, or with an alkali metal phthalimide in order to obtain a product of the formula

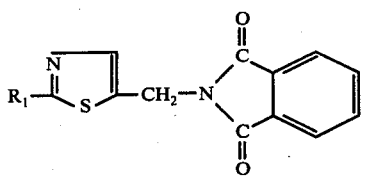

or one of its acid addition salts with a strong mineral or organic acid, isolating either the said complex or the said product or its salts, in the given case, then treating the said complex or the said product with a strong acid in order to obtain the corresponding product of formula I in a salt form. This salt, if desired, can be treated with a base in order to obtain the free base form of the product of formula I, which in turn can be obtained as the acid addition salt by the action of a mineral or organic acid preferably a non-toxic, pharmaceutically-acceptible acid.

More particularly, the present invention also includes a process for the production of the compounds of formula I, wherein $R_2$ and $R_3$ are hydrogen comprising the steps of reacting a thiazole selected from the group consisting of a compound having the formula

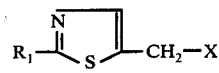

wherein $R_1$ represents an alkyl having from 1 to 6 carbon atoms and X represents a halogen selected from the group consisting of chlorine and bromine, and its acid addition salts with a strong mineral or organic acid, with a compound selected from the group consisting of hexamethylene tetramine, and an alkali metal phthalimide, hydrolyze the reaction product with a strong mineral acid and recovering said 5-thiazole-methane-amine.

The preferred conditions for the above process to produce the product of the invention where $R_2 = R_3 =$ hydrogen are the following:

The reaction of the said thiazole with hexamethylene tetramine is conducted in the presence of an inert organic solvent, such as, for example, chloroform, benzene, toluene, ethyl ether, tetrahydrofuran, cyclohexane, etc.

The alkali metal phthalimide utilized can be, for example, potassium phthalimide, sodium phthalimide or lithium phthalimide.

The reaction of said thiazole with the alkali metal phthalimide is conducted in the presence of an inert organic solvent, such as, for example, dimethylformamide, chloroform, benzene, toluene, ethyl ether, tetrahydrofuran, cyclohexane, etc.

The reaction is conducted at a temperature between room temperature and the reflux temperature of the reaction media.

The salt of the thiazole can be a salt of a strong mineral or organic acid, such as, for example, the hydrochloride, the sulfate, the nitrate, the phosphate, the methanesulfonate, the ethanesulfonate, etc.

When the salt of the thiazole is reacted, an excess of the hexamethylene tetramine or the alkali metal phthalimide is employed.

The strong mineral acid employed for the hydrolysis is preferably, hydrochloric acid, hydrobromic acid, phosphoric acid or sulfuric acid.

The hydrolysis is effected in the presence of an organic solvent, preferably a lower alkanol such as methanol, ethanol, propanol, etc.

When the free base of the said 5-thiazole-methane-amine is desired, the base used to treat the acid addition salt is, for example, an alkali metal hydroxides or carbonates, such as sodium hydroxide, potassium hydroxide, sodium carbonate, potassium carbonate, and ammonium hydroxide.

(B) Compounds of formula I, as well as their acid addition salts with mineral or organic acids, in which at least one of $R_2$ and $R_3$ is other than hydrogen, can be prepared by reacting a product of formula II

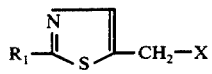   II in which $R_1$ represents alkyl having from 1 to 6 carbon atoms and X represents chlorine or bromine, or one of its acid addition salts with strong mineral or organic acids, with a product of formula III

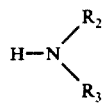   III in which $R_2$ and $R_3$ have the above meanings, in order to obtain a product of the formula I, either the free base or an acid addition salt which, if desired, can be treated with a base to obtain the free base form of a product of formula I, which, if desired can be obtained as an acid addition salt by the action of a mineral or organic acid, preferably a non-toxic, pharmaceutically-acceptible acid.

More particularly, the present invention also includes a process for the production of compounds of formula I, wherein at least one of $R_2$ and $R_3$ is other than hydrogen, comprising the steps of reacting a thiazole selected from the group consisting of a compound having the formula

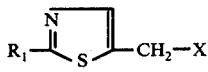

wherein $R_1$ represents an alkyl having from 1 to 6 carbon atoms and X represents a halogen selected from the group consisting of chlorine and bromine, and its acid addition salts with a strong mineral or organic acid, with an amine compound having the formula

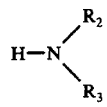

wherein $R_2$ and $R_3$ represent members selected from the group consisting of hydrogen, alkyl having from 1 to 6 carbon atoms, hydroxyalkyl having 1 to 6 carbon atoms, and, taken together, alkylene having up to 5 carbon atoms, azaalkylene having up to 4 carbon atoms, alkylalkylene having up to 5 carbon atoms in the alkylene and 1 to 4 carbon atoms in the alkyl, and alkylazaalkylene having up to 4 carbon atoms in the azaalkylene and 1 to 4 carbon atoms in the alkyl which may be in any position, with the proviso that at least one of $R_2$ and $R_3$ is other than hydrogen, and recovering said 5-thiazole-methane-amine.

The preferred conditions for the above process to produce the product of the invention where at least one of $R_2$ and $R_3$ is other than hydrogen, are the following:

The reaction of said thiazole with said amine compound is conducted in the presence of an inert organic solvent, such as, for example, benzene, toluene, tetrahydrofuran, xylene, ethyl ether, methanol, ethanol, propanol etc.

The reaction is conducted at a temperature between room temperature and the reflux temperature of the reaction media.

The salt of the thiazole can be a salt of a strong mineral or organic acid, such as, for example, the hydrochloride, the sulfate, the nitrate, the phosphate, the methanesulfonate, the ethanedisulfonate, etc.

When the salt of the thiazole is reacted, an excess of the amine compound is employed.

When the free base of the said 5-thiazole-methane-amine is desired, the base used to treat the acid addition salt is, for example, an alkali metal hydroxide or carbonate such as sodium hydroxide, potassium hydroxide, sodium carbonate potassium carbonate, and ammonium hydroxide.

The 5-thiazole-methane-amines of formula I and their mineral or organic acid addition salts possess interesting pharmacological properties. They have a marked antilipolytic activity. They diminish the amount of plasmatic free fatty acids in the blood. They also have a more or less important hypoglycemiant activity.

These properties justify the application of the 5-thiazole-methane-amines and salts as defined above, in therapeutical application as medicaments. They are very useful in the treatment of warm-blooded animals, particularly in the treatment of acute or chronic hyperlipemia, coronarial insufficiencies, cardiac insufficiencies of atheromatous origin, chronic anginous states, and prediabetic or diabetic conditions.

The present invention also includes pharmaceutical compositions containing, as active principle, one or more of the products of formula I or one or more of their acid addition salts with non-toxic, pharmaceutically-acceptable mineral or organic acids.

These compositions are prepared in such a fashion that they can be administered to the digestive tract or parenterally. They can be solids or liquids and are prepared in the currently utilizable pharmaceutical forms for warm-blooded animals as, for example, simple or sugar-coated tablets, gelules, granules, suppositories, injectable preparations. They are prepared according to the usual methods.

One or more of the active principles can be incorporated with the usual pharmaceutical excipients. The pharmaceutical carrier used in the compositions may be those excipients ordinarily used in medicines, such as talc, gum arabic, lactose, starch, magnesium stearate, cacao butter, aqueous or non-aqueous vehicles, fatty bodies of animal or vegetable origin, paraffinic derivatives, glycols, diverse wetting agents or emulsifiers or preservatives.

The present invention also includes a process for the treatment of hyperlipemia and of diabetes in warm-blooded animals, including humans, comprising administering to warm-blooded animals an effective amount of at least one compound of formula I or its salts with non-toxic, pharmaceutically acceptable acids.

The usual dosology, varied according to the product utilized, the patient and the condition being treated, can be, for example, from 0.75 to 50 mg/kg per day or from 0.05 to 2.5 gm per day in the adult, administered orally.

Certain of the thiazole products of formula II and their acid addition salts with strong mineral or organic acids are novel. These novel intermediates are useful for the preparation of the 5-thiazole-methane-amines of the invention. These novel intermediates are 5-thiazole-methyl halides selected from the group consisting of (1) compounds having the formula

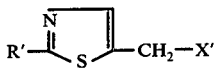

wherein X' represents a halogen selected from the group consisting of chlorine and bromine and, when X' is Cl, R' represents alkyl having from 2 to 6 carbon atoms and, when X' is Br, R' represents alkyl having from 1 to 6 carbon atoms, and (2) its acid addition salts with strong mineral or organic acids.

The novel 5-thiazole-methyl halides above, in which X is chlorine, can be prepared by the action of phosphorus pentachloride on the corresponding alcohol, in the presence of an inert organic solvent.

The novel 5-thiazole-methyl halides above, in which X is bromine, can be prepared by the action of a bromination agent, such as phosphorus tribromide, on the corresponding alcohols.

The acid addition salts of the above novel 5-thiazole-methyl halides are prepared by the action of a strong mineral or organic acid such as those recited above.

The starting alcohols employed in such processes are described, together with a process for their production in Chem. Abstracts, (1963), 58, 2525$b$ and French published U.S. Pat. No. 2,242,094. 2-methyl-5-thiazole-methyl chloride is described, together with a process for its production in Chem. Abstracts (1963), 58, 2525$b$.

2-n-propyl-5-thiazole-methyl chloride can be prepared as indicated above, by the action of phosphorus pentachloride on the corresponding alcohol. 2-n-propyl-5-thiazole-methyl chloride can also be prepared by the action of a chlorination agent, such as thionyl chloride, on the corresponding alcohol, in the presence of an inert organic solvent. An example of such a preparation is given hereafter.

2-n-propyl-5-methylol-thiazole is described in French Pat. No. 2,242,094.

The following examples are illustrative of the invention without being limitative in any manner.

EXAMPLE 1

The Hemisuccinate of 2-methyl-5-thiazole-methane-amine

STEP A: The chloride of 1-[(2-methyl-5-thiazole)-methyl]-3,5,7-triaza-1-azonia-tricyclo/3,3,1,1$^{3,7}$decane 10 gm of 2-methyl-5-thiazole-methyl chloride, were mixed with 180 cc of chloroform and 10 gm of hexamethylene tetramine. The mixture was heated to reflux for 6 hours and brought to room temperature. The precipitate was recovered by vacuum filtering and dried.

15.1 gm of the chloride of 1-[(2-methyl-5-thiazole)-methyl]-3,5,7-triaza-1-azoniatriacyclo/3,3,1,1$^{3,7}$/decane was obtained, having a melting point of 250°–260° C.

STEP B: The hemisuccinate of 2-methyl-5-thiazole-methane-amine

The 15.1 gm of the complex obtained in Step A were mixed with 100 cc of ethanol and 30 cc of concentrated hydrochloric acid. The mixture was heated slightly until complete dissolution and then maintained for 16 hours under agitation at room temperature. The solution was concentrated. The residue was taken up in 80 cc of water and 12N sodium hydroxide was added until a pH of between 12 and 13 was attained.

The aqueous solution was extracted with chloroform. The extracts were combined, dried, filtered and concentrated. 6.2 gm of a raw product were obtained. This raw product was taken up in ethyl ether and sufficient solution of 10% of succinic acid in methanol was added to give a pH of 7. The precipitate was vacuum filtered and dried. 5.5 gm of crystals were obtained, which were recrystallized from isopropanol. 4.6 gm of the hemisuccinate of 2-methyl-5-thiazole-methane-amine were obtained, melting at 180° C.

Analysis: (C$_7$H$_{11}$N$_2$O$_2$S): Calculated: 44.9%, C; 5.92%, H; 14.96%, N; 17.12%, S. Found: 44.8%, C; 6.0%, H; 14.7%, N; 17.4%, S.

EXAMPLE 2

The Acetate of N,2-dimethyl-5-thiazole-methane-amine

The nitrate of 2-methyl-5-thiazole-methyl chloride was prepared by the addition of a solution of 5N nitric acid in ethyl acetate to an ether solution of 2-methyl-5-thiazole-methyl-chloride, melting at 100°–102° C. 7.5 gm of this nitrate were mixed with 100 cc of a 10% solution of monomethyl amine in benzene. The mixture was maintained under agitation for a period of 2 hours and then concentrated. The residue was taken up in 250 cc of diluted ammonia and extracted with methylene chloride. The extracts were combined, washed with water, dried, filtered and concentrated to dryness. 4.8 gm of a raw product were obtained. 4.5 gm of this raw product were dissolved in 100 cc of ethyl ether. Acetic acid was added thereto to a pH of 2 to 3. The precipitate was vacuum filtered, washed with ether and dried. 2.3 gm of crystals were obtained, which were recrystallized from ethyl acetate.

2.1 gm of the acetate of N,2-dimethyl-5-thiazole-methane-amine were obtained, melting at 108° C.

Analysis: (C$_8$H$_{14}$N$_2$O$_2$S): Calculated: 47.50%, C; 6.98%, H; 13.85%, N; 15.85%. S. Found: 47.4%, C; 7.1%, H; 13.7%, N; 15.7%, S.

EXAMPLE 3

The Maleate of N,N,2-trimethyl-5-thiazole-methane-amine 10 gm of the nitrate of 2-methyl-5-thiazole-methyl chloride obtained as in Example 2, were mixed with 50 cc of benzene. Then slowly 45 cc of a benzenic solution containing 33% of dimethylamine were added thereto. The mixture was agitated over night and then concentrated. The residue was taken up in concentrated ammonia solution. The solution was extracted with methylene chloride. The extracts were combined, dried, filtered and concentrated. 10 gm of a raw product were obtained. This raw product was dissolved in 100 cc of ethyl ether. 100 cc of a saturated maleic acid solution in ethyl acetate was added and the mixture was iced. The crystals obtained were vacuum filtered and dried. 8.6 gm of crystals were recovered and recrystallized from ethyl acetate.

8.1 gm of the maleate of N,N,2-trimethyl-5-thiazole-methane-amine were obtained, melting at 118° C.

Analysis: (C$_{11}$H$_{16}$N$_2$O$_4$S): Calculated: 48.52%, C; 5.92%, H; 10.29%, N; 11.77%, S; 23.50%, O. Found: 48.6%, C; 5.9%, H; 10.3%, N; 11.9%, S; 23.5%, O.

EXAMPLE 4

The Dinitrate of N,N-bis-(β-hydroxyethyl)-2-methyl-5-thiazole-methane-amine 10 gm of the nitrate of 2-methyl-5-thiazole-methyl chloride obtained as in Example 2, were mixed with 50 cc of ethanol. A solution of 20 gm of diethanolamine in 50 cc of ethanol was added thereto while agitating. The mixture was agitated for 3 days, then concentrated to dryness. The residue was taken up in 50 cc of distilled water and brought to an alkaline pH with 12N sodium hydroxide solution. This solution was saturated with sodium chloride and then extracted with ethyl acetate. The extracts were combined, dried and concentrated. 9 gm of raw product were obtained. This product was dissolved in 100 cc of ethyl acetate and 50 cc of a solution of 2 cc of nitric acid in 98 cc of ethyl acetate was added thereto. The crystals obtained were vacuum filtered, washed with ether and dried. 10.9 gm of crystals were obtained, which were recrystallized from ethanol.

7.6 gm of dinitrate of N,N-bis(β-hydroxyethyl)-2-methyl-5-thiazole-methane-amine were obtained, melting at 120° C.

Analysis: ($C_9H_{18}N_4O_8S$): Calculated: 31.58%, C; 5.30%, H; 16.36% N; 9.37%, S. Found: 31.7%, C; 5.3%, H; 16.1%, N; 9.4%, S.

EXAMPLE 5

The Hemisuccinate of 2-n-propyl-5-thiazole-methane-amine

STEP A: 2-n-propyl-5-thiazole-methyl chloride 17 cc of thionyl chloride were added to a solution cooled to 10° to 12° C of 17.5 gm of 2-n-propyl-5-methylol-thiazole in 150 cc of benzene. The mixture was agitated at room temperature for 30 minutes, then poured on 300 cc of ice. Sufficient of an aqueous saturated solution of sodium carbonate was added thereto to give a pH of 7 to 8. This mixture was extracted with ethyl acetate. The extracts were combined, dried and concentrated under reduced pressure. 20 gm of 2-n-propyl-5-thiazole-methyl chloride were obtained in the form of an oil. This was utilized as such in Step B.

The 2-n-propyl-5-thiazole-methyl chloride was isolated in the form of the hemiethanedisulfonate by dissolving the raw product in ethyl acetate and adding thereto a saturated solution of ethanedisulfonic acid in isopropanol, with recrystallization of the separated crystals from isopropanol. The hemiethanedisulfonate of 2-n-propyl-5-thiazole-methyl chloride obtained melted at 132° C.

Analysis: ($C_8H_{13}Cl\ N\ O_3S_2$): Calculated: 35.49%, C; 4.84%, H, 5.17%, N; 13.09%, Cl; 23.68%, S. Found: 35.6%, C; 5.1%, H; 5.0%, N; 12.9%, Cl; 23.6%, S.

STEP B: 2-[(2-n-propyl-thiazol-5-yl)-methyl]-1H-isoindole-1,3-(2H)-dione 10 gm of the raw product obtained in Step A and 10.6 gm of the potassium salt of 1H-isoindole-1,3-(2H)-dione (potassium phthalimide) were mixed in 25 cc of dimethylformamide. The mixture was heated to reflux for 30 minutes, then cooled to room temperature and water was added thereto. The crystals which separated were vacuum filtered, washed with water, and dissolved in ethyl acetate. The solution was dried and concentrated under reduced pressure.

15.1 gm of 2-[(2-n-propyl-thiazol-5-yl)-methyl]-1H-isoindole-1,3-(2H)-dione were obtained, melting at 72° C.

STEP C: The hemisuccinate of 2-n-propyl-5-thiazole-methane-amine

The crystals obtained in Step B were dissolved in 75 cc of concentrated hydrochloric acid. The mixture was heated to reflux for 3 hours and then iced. A concentrated sodium hydroxide solution was added thereto to give a pH of 12 to 13. The mixture was extracted with ethyl acetate. The extracts were combined, dried and concentrated under reduced pressure. 7.5 gm of raw product were obtained, which was dissolved in ethyl acetate. A 10% solution of succinic acid in methanol was added until the pH reached 7. The mixture was iced and the crystals were filtered under reduced pressure.

The material was recrystallized from isopropanol and 6 gm of the hemisuccinate of 2-n-propyl-5-thiazole-methane-amine were obtained, melting at 120° C.

Analysis: ($C_9H_{15}N_2O_2S$): Calculated: 50.21%, C; 7.02%, H; 13.01%, N; 14.89%, S. Found: 50.1%, C; 7.2%, H; 13.0%, N; 15.2%, S.

EXAMPLE 6

The Hemiethanedisulfonate of 2-methyl-5-(piperidin-1-yl-methyl)-thiazole 8 gm of the nitrate of 2-methyl-5-thiazole-methyl chloride (obtained as in Example 2) was introduced into a mixture of 12.8 gm of piperidine in 160 cc of ethanol. The mixture was agitated at room temperature for 60 hours. Thereafter the solvent was evaporated under reduced pressure. The residue was dissolved in a minimum amount of water and an ammonia solution was added to give an alkaline pH. The mixture was extracted with ethyl acetate. The extracts were combined, washed with water, dried and concentrated under reduced pressure. 7.3 gm of raw product was obtained. This raw product was dissolved in ethyl acetate and a solution of 3.4 gm of ethanedisulfonic acid in 73 cc of ethyl acetate was added thereto. The mixture was iced for 30 minutes. The precipitate was filtered, washed with ethyl acetate and then with ethyl ether.

The crystals obtained were recrystallized from isopropanol and 7.4 gm of the hemiethanedisulfonate of 2-methyl-5-(piperidin-1-yl-methyl)-thiazole were obtained melting at 202° C.

Analysis: ($C_{11}H_{19}N_2O_3S_2$): Calculated: 45.33%, C; 6.57%, H; 9.61%, N; 22.01%, S. Found: 45.4%, C; 6.7%, H; 9.3%, N; 22.1%, S.

EXAMPLE 7

2-methyl-5-(4-methyl-piperazin-1-yl-methyl)-thiazole 9.4 gm of the nitrate of 2-methyl-5-thiazole-methyl chloride (obtained as in Example 2) was introduced into a mixture of 16.6 gm of N-methyl-piperazine in 180 cc of ethanol. The mixture was agitated for 60 hours at room temperature. Thereafter the solvent was evaporated under reduced pressure. The residue was dissolved in a minimum of water and a concentrated ammonia solution was added to give an alkaline pH. The mixture was extracted with ethyl acetate. The extracts were combined, dried and concentrated under reduced pressure.

An oil was obtained which was purified by distillation under reduced pressure. 9.3 gm of 2-methyl-5-(4-methyl-piperazin-1-yl-methyl)-thiazole were obtained, having a boiling point at 0.4 mm of mercury of 84°–85° C.

Analysis: ($C_{10}H_{17}N_3S$): Calculated: 56.83%, C; 8.10%, H; 19.88%, N; 15.17%, S. Found: 56.6%, C; 8.2%, H; 19.6%, N; 15.1%, S.

EXAMPLE 8

Pharmaceutical Compositions (a) Tablets

Tablets were prepared corresponding to the following recipe:
 The hemisuccinate of 2-methyl-5-thiazole-methane-amine — 300 mg
 Excipient sufficient for a tablet of — 500 mg
 The excipient can include lactose, wheat starch, modified starch, rice starch, magnesium stearate, talc, etc.

(b) Gelules

Gelules were prepared corresponding to the following recipe:
 The acetate of N,2-dimethyl-5-thiazole-methane-amine — 300 mg
 Excipient for a gelule containing — 350 mg
 The excipient can include talc, magnesium stearate, "Aerosil O", etc. "Aerosil" is a finely divided silicic acid.

EXAMPLE 9

Pharmaceutical Compositions (a) Tablets

Tablets were prepared corresponding to the following recipe:
 The hemisuccinate of 2-n-propyl-5-thiazole-methane-amine — 100 mg
 Excipient sufficient for a tablet of — 250 mg.
 The excipient can include the same ingredients as listed above in Example 8.

(b) Gelules

Gelules were prepared corresponding to the following recipe:
 The hemisuccinate of 2-n-propyl-5-thiazole-methane-amine — 100 mg
 Excipient for a gelule containing — 150 mg
 The excipient can include the same ingredients as listed above in Example 8.

EXAMPLE 10

Pharmacological data

A. Acute toxicity

The acute toxicity was determined on groups of 10 mice weighing between 18 and 22 g and the product was administered intraperitoneally as a suspension in carboxymethylcellulose. The animals were observed for one week and the average lethal dose ($DL_{50}$) was determined. The results are reported in Table I.

TABLE I

| Product of Example | $DL_{50}$ in mg/kg |
|---|---|
| 1 | > 1000 |
| 2 | ≃ 700 |
| 3 | ≃ 450 |
| 4 | ≃ 900 |
| 5 | ≃ 650 |

TABLE I-continued

| Product of Example | $DL_{50}$ in mg/kg |
|---|---|
| 7 | ≃ 500 |

B. Antilipolytic Activity: Determination of Plasmatic Free Fatty Acids in the Blood Male rats of the Sprague Dawley SPF strain weighing about 180 to 200 gm were starved for 24 hours and then were given the product orally. One hour after the oral administration, the animals were killed by carotidienne section and samples of the blood were obtained to determine the amount of free fatty acids. The extraction of the free fatty acids was made by the technique of Dole [J. Clin. Invest., Vol. 38 (1959), p. 1544–1554] as modified by Trout et al. [J. Lipid. Res., Vol. 1 (1960) p. 199–202]. The plasmatic extract freed of phospholipids was colorimetrically examined by the method of Anthonis [J. Lipid. Res., Vol. 6 (1965), p. 307–312]. Under these test conditions, the dose of the products which reduced by 50% the level of free fatty acids in the treated animals as compared to the controls ($DA_{50}$) was determined. The results are reported in Table II.

TABLE II

| Product of Example | $DA_{50}$ in mg/kg |
|---|---|
| 1 | ≃ 0.8 |
| 2 | ≃ 4 |
| 3 | ≃ 5 |
| 5 | ≃ 8 |

These results show that the products of Examples 1,2,3 and 5 cause a clear reduction of the amount of plasmatic free fatty acids in the blood.

C. Hypoglycemiant Activity: Determination of Glycemia

Male rats of the Sprague Dawley SPF strain weighing between 180 and 200 gm were starved for 24 hours and were then given the test product orally. One hour after the administration, the animals were killed by carotidienne section and blood samples were taken to determine the glycemia. The seric extract was treated by the enzymatic (glucose-oxydase) method of Boehringer and the percent of reduction of glycemia as compared to the controls was determined for each dose of the product administered. The results are reported in Table III.

TABLE III

| Product of Example | Dose mg/kg | Percentage of reduction of the glycemia |
|---|---|---|
| 5 | 5 | −12% |
|  | 10 | −14% |
|  | 20 | −27% |

The preceeding specific embodiments are illustrative of the practice of the invention. It is to be understood however, that other expedients known to those skilled in the art or disclosed herein, may be employed without departing from the spirit of the invention or the scope of the appended claims.

We claim:

1. A 5-thiazole-methane-amine selected from the group consisting of (1) compounds having the formula

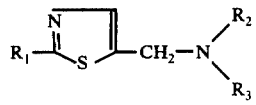

wherein $R_1$ represents an alkyl having from 1 to 6 carbon atoms and $R_2$ and $R_3$ represent members selected from the group consisting of hydrogen, alkyl having from 1 to 6 carbon atoms, hydroxyalkyl having 1 to 6 carbon atoms, and taken together with the nitrogen atom form a member selected from the group consisting of pyrrolidin-1-yl, imidazolidin-1-yl, 3-methyl-imidazolidin-1-yl, 3-ethyl-imidazolidin-1-yl, pyrazolidin-1-yl, 2-methyl-pyrazolidin-1-yl, piperidin-1-yl, piperazin-1-yl, 4-methyl-piperazin-1-yl, 4-ethyl-piperazin-1-yl, 4-propyl-piperazin-1-yl, 4-butyl-piperazin-1-yl, hexahydropyridazin-1-yl, 2-methyl-hexahydro-pyridazin-1-yl, hexahydropyrimidin-1-yl and 3-methyl-hexahydro-pyrimidin-1-yl and (2) its acid addition salts with non-toxic, pharmaceutically-acceptable acids.

2. A compound of claim 1 wherein $R_2$ and $R_3$ represent members selected from the group consisting of hydrogen, methyl, ethyl and hydroxyethyl.

3. A compound of claim 1 wherein $R_1$ represents a member selected from the group consisting of methyl, ethyl and propyl and $R_2$ and $R_3$ represent members selected from the group consisting of hydrogen and methyl.

4. A compound of claim 1 wherein $R_2$ and $R_3$ represent members selected from the group consisting of pentamethylene and N-methyl-3-azapentamethylene.

5. A compound of claim 1 selected from the group consisting of 2-methyl-5-thiazole-methane-amine ($R_1 = CH_3$, $R_2 = R_3 = H$) and its non-toxic, pharmaceutically acceptable acid addition salts.

6. A compound of claim 1 selected from the group consisting of N,2-dimethyl-5-thiazole-methane-amine ($R_1 = R_2 = CH_3$, $R_3 = H$) and its non-toxic, pharmaceutically acceptable acid addition salt.

7. A compound of claim 1 selected from the group consisting of N,N,2-trimethyl-5-thiazole-methane-amine ($R_1 = R_2 = R_3 = CH_3$) and its non-toxic, pharmaceutically acceptable acid addition salts.

8. A compound of claim 1 selected from the group consisting of N,N-bis-($\beta$-hydroxyethyl)-2-methyl-5-thiazole-methane-amine ($R_1 = CH_3$, $R_2 = R_3 = CH_2CH_2OH$) and its non-toxic, pharmaceutically acceptable addition salts.

9. A compound of claim 1 selected from the group consisting of 2-n-propyl-5-thiazole-methane-amine ($R_1 = CH_2CH_2CH_3$, $R_2 = R_3 = H$) and its non-toxic, pharmaceutically acceptable acid addition salts.

10. A compound of claim 1 selected from the group consisting of 2-methyl-5-(piperidin-1-yl-methyl)-thiazole ($R_1 = CH_3$, $R_2 + R_3 = CH_2-CH_2-CH_2-CH_2-CH_2-$) and its non-toxic, pharmaceutically acceptable acid addition salts.

11. A compound of claim 1 selected from the group consisting of 2-methyl-5-(4-methyl-piperazin-1-yl)-thiazole

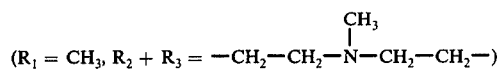

and its non-toxic pharmaceutically acceptable acid addition salts.

12. A method for the treatment of hyperlipemia and diabetis in warm-blooded animals suffering from the same comprising administrating to said warm-blooded animals an amount to lower the level of plasmatic free fatty acids in the blood and hypoglycemically effective amount of at least one compound of claim 1.

13. The method of claim 12 wherein said compound is the hemisuccinate of 2-methyl-5-thiazole-methane-amine.

14. A composition for treating hyperlipemia and diabetes comprising an amount of at least one compound of claim 1 to lower the level of plasmatic free fatty acids in the blood and induce hypoglycemia and an inert pharmaceutical carrier.

* * * * *